(12) United States Patent
Thenappan et al.

(10) Patent No.: US 6,268,540 B1
(45) Date of Patent: Jul. 31, 2001

(54) CATALYST AND PROCESS FOR THE FLUORINATION OF HYDROHALOMETHANES

(75) Inventors: Alagappan Thenappan, Cheektowaga; Addison Miles Smith, Amherst; Jeffrey Warren McKown, East Aurora; Robert Louis Bell, Amherst, all of NY (US)

(73) Assignee: AlliedSignal Inc., Morris Township, NJ (US)

( * ) Notice: Subject to any disclaimer, the term of this patent is extended or adjusted under 35 U.S.C. 154(b) by 0 days.

(21) Appl. No.: 08/672,005

(22) Filed: Jun. 24, 1996

(51) Int. Cl.$^7$ .................................................. C07C 17/00
(52) U.S. Cl. .................... 570/167; 423/466; 502/224; 502/227; 502/228
(58) Field of Search .................... 570/167; 423/466; 502/224, 227, 228

(56) References Cited

U.S. PATENT DOCUMENTS

| 3,929,601 | * 12/1975 | Asprey et al. ............... 423/466 UX |
| 5,202,506 | 4/1993 | Kirschner et al. ................... 568/842 |
| 5,202,509 | 4/1993 | Laviron et al. ..................... 570/167 |
| 5,283,382 | 2/1994 | Nappa ................................ 570/168 |
| 5,426,252 | 6/1995 | Sherif ................................ 570/176 |

FOREIGN PATENT DOCUMENTS

| 0 348 190 | 12/1989 | (EP) . |
| 0 415 814 | 8/1990 | (EP) . |
| WO 89/12616 | 12/1989 | (WO) . |
| WO 95/35271 | 12/1995 | (WO) . |

OTHER PUBLICATIONS

Chemical Abstracts, vol. 103, No. 14, p. 114944h, Oct. 1985.*
Chemical Abstracts, vol. 118, No. 12, p. 182011q, May 1993.*
Chemical Abstracts, vol. 73, p. 94206d, Nov. 1970.*
Chemical Abstracts, vol. 106, No. 25, p. 221,099y, Jun. 1987.*
Chemical Abstracts, vol. 68, No. 24, p. 110889h, Jun. 1968.*
Derwent Abstract AN—76–31069X [17], 1997.
Derwent Abstract AN—94–338219 [42], 1997.

* cited by examiner

*Primary Examiner*—Paul F. Shaver
(74) *Attorney, Agent, or Firm*—Colleen D. Szuch

(57) ABSTRACT

The present invention provides catalysts and processes for the fluorination of hydrohalomethanes. In particular, the invention provides a process for the fluorination of hydrohalomethanes using hydrogen fluoride and a Lewis Acid catalyst. More specifically, catalysts and a process for the fluorination of dichloromethane are provided.

33 Claims, 4 Drawing Sheets

# CATALYST AND PROCESS FOR THE FLUORINATION OF HYDROHALOMETHANES

FIELD OF THE INVENTION

The present invention relates to catalysts and processes for the fluorination of hydrohalomethanes. In particular, the invention provides a process for the fluorination of hydrohalomethanes using hydrogen fluoride and a Lewis Acid catalyst.

BACKGROUND OF THE INVENTION

Hydrofluorocarbons, HFC's, are of great interest due to their potential to replace ozone-depleting chlorofluorocarbons, CFC's, and hydrochlorofluorocarbons, HCFC's. For example, an azeotropic mixture of difluoromethane ("HFC-32") and pentafluoroethane ("HFC-125") has been identified as a replacement for chlorodifluoromethane ("HCFC-22") in refrigeration and air-conditioning applications. Binary mixtures of HFC-32 and 1,1,1,2-tetrafluoroethane ("HFC-134a") and ternary mixtures of HFC-32, HFC-134a, and HFC-125 also have been proposed as HCFC-22 replacements.

Methods for the production of HFC's, such as HFC-32, are known. For example, U.S. Pat. No. 5,426,252 discloses a catalytic hydrodechlorination process in which HCFC-22 and dichlorodifluoromethane ("CFC-12") are reacted with hydrogen in the presence of a palladium-based catalyst to produce HFC-32. This process is disadvantageous in that it both requires formation of the feed materials from the corresponding chlorocarbons and has low conversion and poor selectivity in the hydrogenation step.

Another method is exemplified in U.S. Pat. Nos. 5,446,215 and 5,463,139, which disclose the reaction of formaldehyde and hydrogen fluoride in the presence of a solvent to produce bis(fluoromethyl ether) which is then dehydrated to yield HFC-32. The multiple steps of this process and its requirement of intermediate purification makes this method economically disadvantageous.

U.S. Pat. No. 5,495,057 discloses the liquid phase preparation of HFC-32 from HCC-30, hydrogen fluoride and antimony pentachloride at 70° C. to 90° C. and 11 to 12 kg/cm² pressure. This process is disadvantageous because the use of antimony pentahalide catalyst and a hydrogen fluoride system is extremely corrosive to most metals and often, the antimony pentahalide is reduced to less active antimony trihalide in the fluorination reactions.

Thus, a need exists for an efficient and economical process for the fluorination of hydrohalomethanes, including HCC-30.

DESCRIPTION OF THE INVENTION AND ITS PREFERRED EMBODIMENTS

Figure 1:
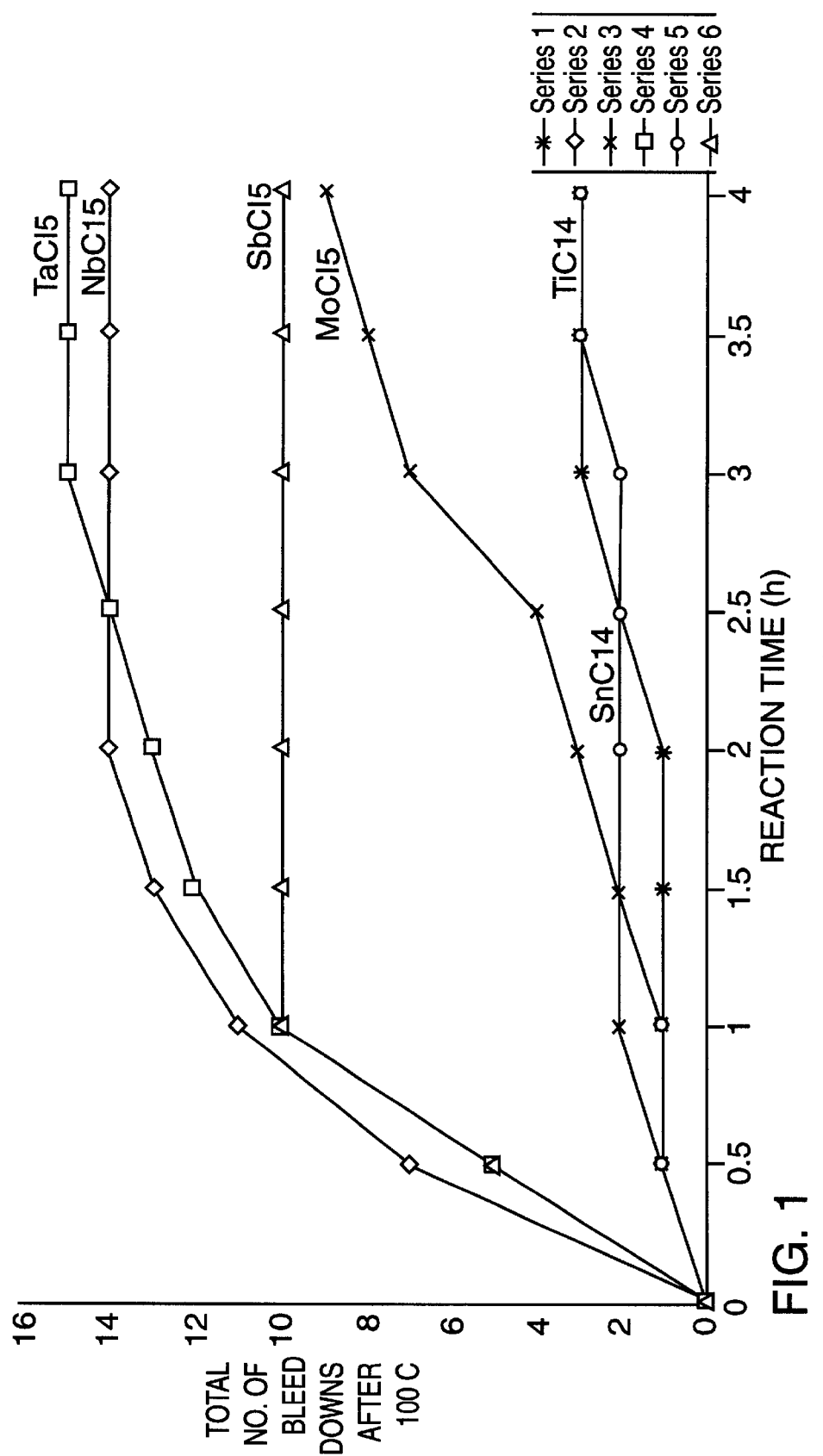
FIG. 1 compares the hydrohalomethane productivity rate of different catalysts.
Figure 2:
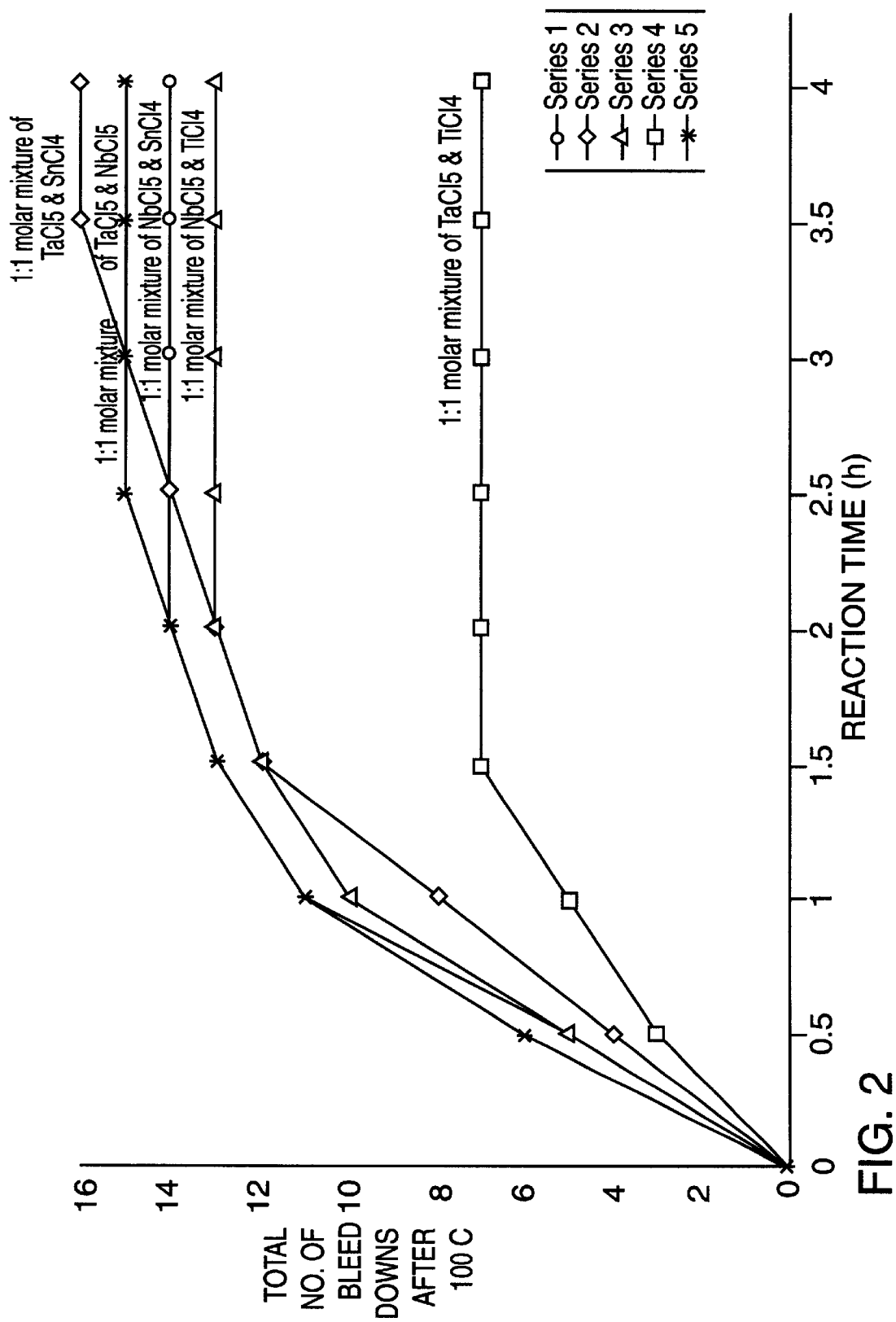
FIG. 2 depicts the hydrohalomethane productivity rate of the catalysts of the invention.
Figure 3:
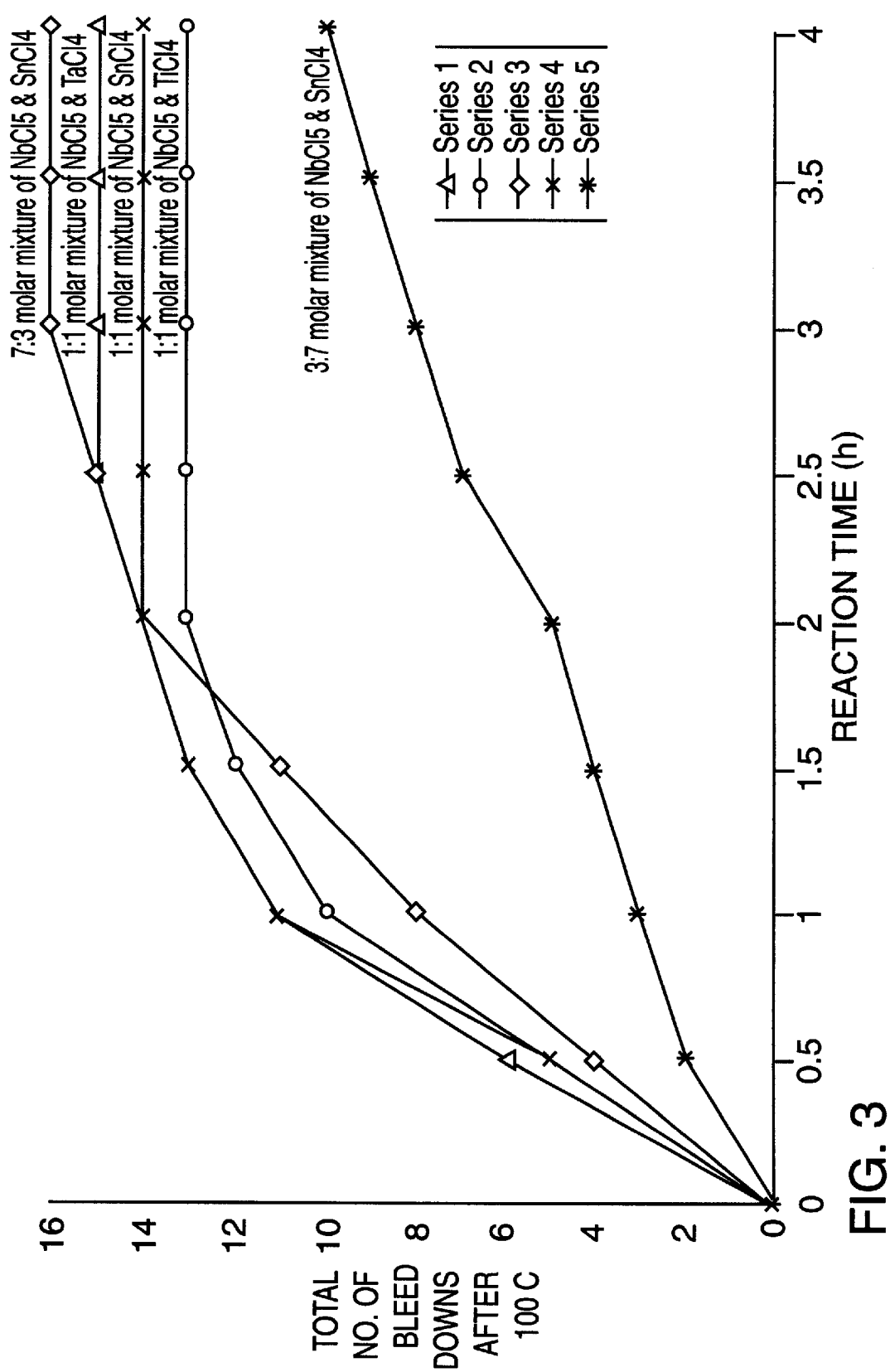
FIG. 3 depicts the effect on the hydrohalomethane productivity rate of varying concentration of niobium pentachloride in catalyst mixtures.
Figure 4:
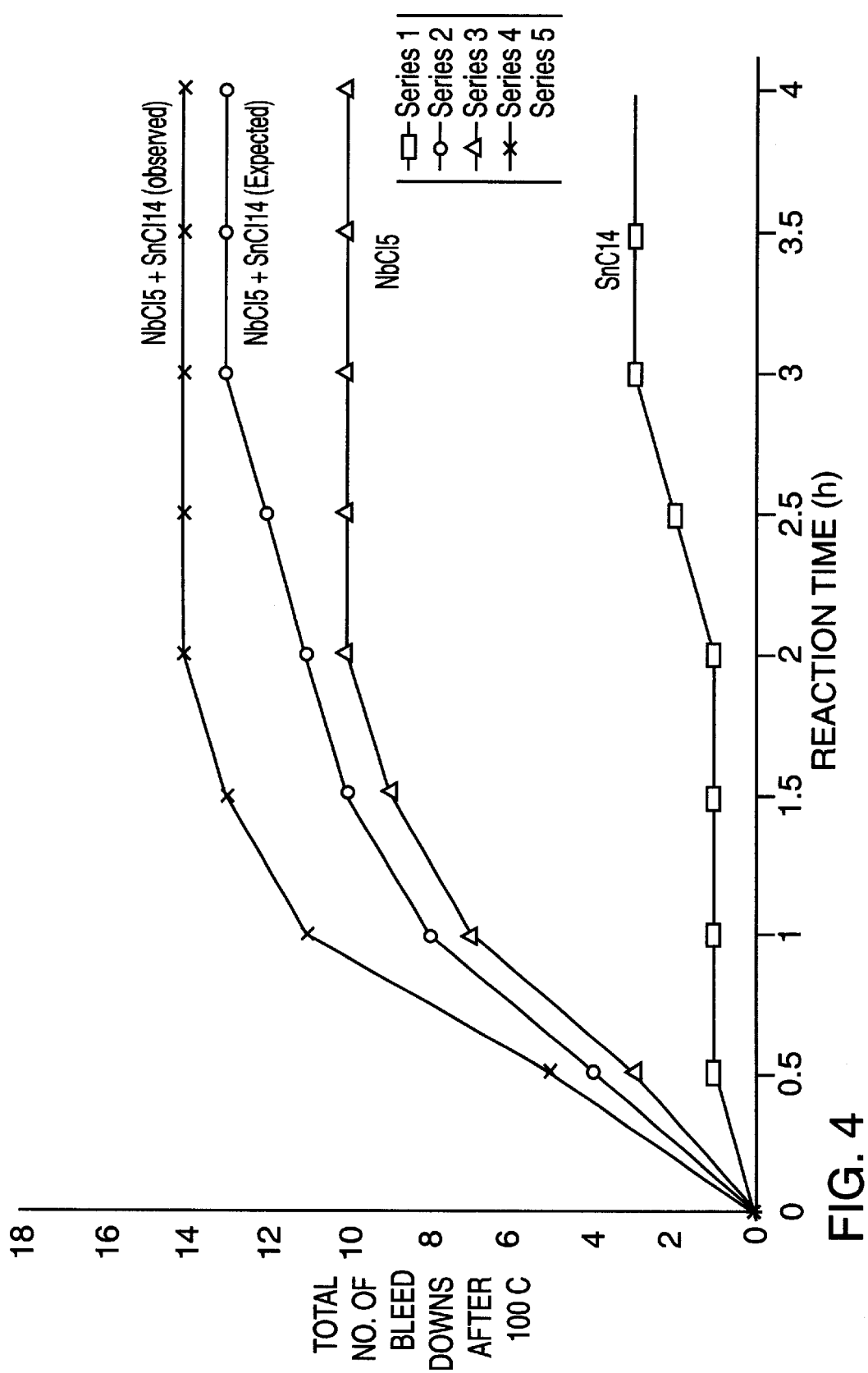
FIG. 4 depicts the hydrohalomethane productivity rate of a catalyst of the invention versus known catalysts.

The present invention provides catalysts for the liquid phase fluorination of hydrohalomethanes, such as HCC-30.

The catalysts of the invention are: (i) pentavalent molybdenum halides of the formula $MoCl_{5-z}F_z$ wherein z is 0 to 5; ii) mixtures of pentavalent niobium halides of the formula $NbCl_{5-y}F_y$ wherein y is 0 to 5, with tetravalent tin halides of the formula $SnCl_{4-n}F_n$ wherein n is 0 to 4; (iii) mixtures of pentavalent niobium halides of the formula $NbCl_{5-y}F_y$ wherein y is 0 to 5 with tetravalent titanium halides of the formula $TiCl_{4-m}F_m$ wherein m is 0 to 4; (iv) mixtures of pentavalent tantalum halides of the formula $TaCl_{5-x}F_x$ wherein x is 0 to 5 with tetravalent tin halides of the formula $SnCl_{4-n}F_n$ wherein n is 0 to 4; (v) mixtures of pentavalent tantalum halides of the formula $TaCl_{5-x}F_x$ wherein x is 0 to 5 with tetravalent titanium halides of the formula $TiCl_{4-m}F_m$ wherein m is 0 to 4; and (vi) mixtures of pentavalent niobium halides of the formula $NbCl_{5-y}F_y$ wherein y is 0 to 5 with pentavalent tantalum halides of the formula $TaCl_{5-x}F_x$ wherein x is 0 to 5. For purposes of the invention, the term halide is to be understood to include halides and mixed halides.

In another embodiment, the invention provides a liquid phase process for hydrohalomethane fluorination that comprises contacting a hydrohalomethane with an effective amount of hydrogen fluoride in the presence of a catalytically effective amount of a catalyst of the invention at a temperature from about 25° C. to about 200° C. in order to produce a fluorinated product mixture. In yet another embodiment of the invention, a process for the production of HFC-32 is provided that comprises contacting HCC-30 with at least two equivalents of hydrogen fluoride in the presence of a catalytically effective amount of a catalyst of the invention at a temperature from about 25° C. to about 200° C. in order to produce a HFC-32 product mixture. The catalysts and processes of the invention exhibit very high conversion and excellent selectivity and are less corrosive of reactors in comparison to known hydrohalomethane fluorination catalysts and reactions.

WO 89/12616 discloses liquid and vapor phase processes for producing fluorinated alkanes from halogenated alkanes using hydrogen fluoride and a tantalum chloride or bromide catalyst. European Patent Application 348 190 discloses a niobium chloride or bromide catalyzed process for preparing fluorinated alkanes from halogenated alkanes and hydrogen fluoride. In neither of these applications is there a disclosure that the use of these catalysts results in a less reactor-corrosive reaction. Further, it has been reported that tantalum and niobium pentachlorides do not exhibit catalytic activity towards the addition of hydrogen fluoride to unsaturated olefins. See A. E. Feiring, "Chemistry in Hydrogen Fluoride v. Catalysts for Reaction of Hydrogen Fluoride With Halogenated Olefins", 13 J. Fluorine Chem., 7–18 (1979). Therefore, based on the information in the prior art, the discovery that the fluorination of hydrohalomethanes with hydrogen fluoride in the presence of the catalysts of the invention, which fluorination exhibits high conversion and selectivity and is less reactor-corrosive, is surprising.

The reactor used in the processes of the invention may be any suitable reactor constructed of material resistant to attack by the reactants including, without limitation, stainless steel, nickel, MONEL™, INCONEL™, and HASTELLOY-C™, and reactors lined with or made from resins including, without limitation, polytetrafluoroethylene, polychlorotrifluoroetbylene, polyvinylidene chloride, and polyfluoroalkoxy substituted polymers.

The hydrohalomethanes that may be fluorinated by the processes of the invention are of the formula $CH_xCl_yF_z$ wherein x is 1, 2 or 3, y is 1, 2 or 3, z is 0 or 1, and the sum of x, y, and z is 4. Examples of such hydrohalomethanes include, without limitation, chloromethane, HCC-30, trichloromethane, chlorofluoromethane, and dichlorofluoromethane. Preferably, HCC-30 is used. All of the hydrohalomethanes useful in the invention are commercially available.

The catalysts of the invention are of the following groups: (i) pentavalent molybdenum halides of the formula $MoCl_{5-z}F_z$ wherein z is 0 to 5; (ii) mixtures of pentavalent niobium halides of the formula $NbCl_{5-y}F_y$ wherein y is 0 to 5, with tetravalent tin halides of the formula $SnCl_{4-n}F_n$ wherein n is 0 to 4; (iii) mixtures of pentavalent niobium halides of the formula $NbCl_{5-y}F_y$ wherein y is 0 to 5 with tetravalent titanium halides of the formula $TiCl_{4-m}F_m$ wherein m is 0 to 4; (iv) mixtures of pentavalent tantalum halides of the formula $TaCl_{5-x}F_x$ wherein x is 0 to 5 with tetravalent tin halides of the formula $SnCl_{4-n}F_n$ wherein n is 0 to 4; (v) mixtures of pentavalent tantalum halides of the formula $TaCl_{5-x}F_x$ wherein x is 0 to 5 with tetravalent titanium halides of the formula $TiCl_{4-m}F_m$ wherein m is 0 to 4 ; and (vi) mixtures of pentavalent niobium halides of the formula $NbCl_{5-y}F_y$ wherein y is 0 to 5 with pentavalent tantalum halides of the formula $TaCl_{5-x}F_x$ wherein x is 0 to 5. In the processes of the invention, preferably catalysts of groups (ii) and (iv) are used. More preferably, catalysts of group (ii) are used.

Preferred catalyst species are mixtures of niobium pentachloride and tantalum pentachloride; mixture of niobium pentachloride and tin tetrachloride; mixtures of niobium pentachloride and titanium tetrachloride; mixtures of tantalum pentachloride and tin tetrachloride; and mixtures of tantalum pentachloride and titanium tetrachloride. More preferred species are mixtures of niobium pentachloride and tantalum pentachloride; mixtures of niobium pentachloride and tin tetrachloride; and mixtures of tantalum pentachloride and tin tetrachloride. Most preferred species are mixtures of niobium pentachloride and tin tetrachloride and mixtures of tantalum pentachloride and tin tetrachloride.

It has been discovered that the catalysts of the invention may be used to produce fluorinated hydrohalomethanes in high conversion and selectivity. Additionally, for the catalysts that are mixtures, it was discovered that fluorination of HCC-30 proceeds with a rate of productivity of HFC-32 that is higher than would be predicted by considering the productivity rates of the mixtures' components separately.

The pentavalent tantalum, niobium and molybdenum halides and tetravalent tin and titanium halides are commercially available. The mixed halides may be generated in situ by reaction with hydrogen fluoride. A catalytically effective amount of catalyst is used, which amount is an amount sufficient to maintain the desired level of catalytic activity in the specific fluorination reaction used. The amount of catalyst used, generally, is an amount from about 2 to about 80 mole percent based on the amount of organics, more preferably from about 5 to about 50 mole percent, and most preferably from about 10 to about 20 mole percent. The catalysts may be supported on any suitable support including, without limitation, activated carbon or alumina. For the group (ii) through group (vi) catalysts, the molar ratio of the components of the mixture used is from about 1:9 to about 9:1, preferably from about 3:7 to about 7:3, most preferably about 1:1.

Because water will react with, and deactivate the catalysts, the reaction is carried out under substantially anhydrous conditions. By substantially anhydrous is meant that the reaction is run under conditions as free from water as is practicable or possible. For example, the reactor may be flushed with nitrogen before charging. Also, the hydrogen fluoride used is commercially available anhydrous hydrogen fluoride having a water content of 0.1 percent or less. An effective amount of hydrogen fluoride is used, which amount, based on reaction stoichiometry, is a mole ratio of hydrogen fluoride to organics that is at least equal to the number of chlorine atoms to be replaced in the hydrohalomethane. Thus, for hydrohalomethanes of the formula $CH_xCl_yF_z$, wherein x is 1, 2 or 3, y is 1, 2 or 3, z is 0 or 1, and the sum of x, y, and z is 4, the amount of hydrogen fluoride used is equal to 4−(x +z). The hydrogen fluoride preferably is used in an amount from about 1 to about 9 times the stoichiometric amount of hydrogen fluoride to hydrohalomethane, more preferably 2 to about 6 times.

The temperature at which the process of the invention is conducted and the residence time of the reaction will depend on the hydrohalomethane and catalyst selected. The reaction, generally, will be conducted at a temperature from about 25° C. to about 200° C., preferably 90° C. to about 140° C. Residence times, generally, will be from about 1 to about 24 hours, preferably from about 2 to about 8 hours.

The reaction pressure is not critical and will vary depending on such factors as the amount of hydrogen fluoride used, the hydrogen chloride generated, and the desired conversion of organics. Convenient operating pressures will range from about 50 to about 600 psig. The pressure may be adjusted by continuously removing hydrogen chloride and volatile products from the reaction mixture through any convenient means, for example by distillation.

The processes of the invention are carried out by contacting the hydrohalomethane compound with hydrogen fluoride in the presence of a catalyst of the invention in order to produce a fluorinated product mixture. Charging of these materials into the reactor may occur in any order. Preferably, the catalyst is charged to the reactor, the reactor cooled, and the hydrohalomethane and hydrogen fluoride are charged. The reaction mixture is then heated to the reaction temperature, during which the mixture may be stirred or otherwise agitated, to produce the fluorinated product mixture.

The fluorinated product may be recovered from the fluorinated product mixture via any known separation method. The recovered fluorinated product may then be purified by any means, such as by distillation, in order to provide a purified product.

The processes of the invention may be carried out in batch or continuous modes. The continuous mode requires the continuous removal of fluorinated product and hydrogen chloride from the reactor as they are formed. Unreacted hydrogen fluoride and under-fluorinated materials, such as chlorofluoromethane in the fluorination of HCC-30, may be recycled to the reactor.

The following illustrative examples will serve to clarify the invention further.

EXAMPLES

Example 1

A 600 mL Hastelloy-C autoclave equipped with a magnetic stir drive was charged with 0.1 mole, 26.0 g $SnCl_4$ and cooled to −20° C. The autoclave was then evacuated and charged with 2.1 moles, 41.4 g anhydrous HF. The contents were cooled to −20° C. and 0.5 moles, 42.5 g HCC-30 were added. The reactor was then connected to a packed column/condenser assembly and the condenser maintained at −5° C. The reaction mixture was heated with stirring to about 130°

C. over 2 hours and maintained at that temperature for an additional 3 hours. During this period, the pressure in the autoclave was maintained between 300–400 psig by periodically venting the pressure in excess of 400 psig. Venting was performed from the condenser's top to an aqueous potassium hydroxide scrubber that was connected in series to two cold traps cooled with dry ice/isopropyl alcohol and liquid nitrogen, respectively. After 5 hours, the reactor was completely vented to the cold traps to give 35.1 g of product mixture. Gas chromatographic analysis of that mixture is reported on Table 1.

Example 2

The procedure of Example 1 was repeated. The reactor was charged with 0.1 mole, 19.0 g $TiCl_4$, 2.09 moles, 41.8 g HF, and 0.5 moles, 42.5 g HCC-30. The reaction mixture was heated with stirring to about 135° C. and maintained and vented as in Example 1 to give 31.6 g product. GC analysis of the mixture is reported on Table 1.

Example 3

The procedure of Example 1 was repeated. The reactor was charged with 0.1 mole, 27.3 g $MoCl_5$, 1.97 moles, 39.4 g HF, and 0.5 moles, 42.5 g HCC-30. The reaction mixture was heated with stirring to 135° C. in 2 hours and maintained at that temperature and vented as in Example 1. Venting yielded 31.6 g product mixture. GC analysis of the mixture is reported on Table 1.

Example 4

The procedure of Example 1 was repeated. The reactor was charged with 0.1 mole, 27.0 g $NbCl_5$, 2.23 moles, 44.5 g HF, and 0.5 moles, 42.5 g HCC-30. The reaction mixture was heated to 130° C., maintained and vented as in Example 1. Venting yielded 34.2 g of product mixture. GC analysis of the mixture is reported on Table 1.

Example 5

The procedure of Example 1 was repeated. The reactor was charged with 0.1 mole, 35.0 g $TaCl_5$, 1.91 moles, 38.1 g HF, and 0.5 moles, 42.5 g HCC-30. The reaction mixture was heated to 130° C. and maintained and vented as in Example 1. 33.4 g product mixture was recovered. GC analysis of the mixture is reported on table 1.

Example 6

The procedure of Example 1 was repeated. The reactor was charged with 0.03 moles, 10.7 g $TaCl_5$, and 0.07 moles, 18.9 g $NbCl_5$, 2.21 moles, 44.1 g HF, and 0.5 moles, 42.5 g HCC-30. The reaction mixture was heated to 120° C. and maintained and vented as in Example 1. 29.2 g product mixture was recovered. GC analysis of the mixture is reported on Table 1.

Example 7

The procedure of Example 1 was repeated. The reactor was charged with 0.07 moles, 18.9 g $NbCl_5$, 0.03 moles, 7.8 g $SnCl_4$, 2.02 moles, 40.3 g HF, and 0.5 moles, 42.5 g HCC-30. The reaction mixture was heated to 120° C. and maintained and vented as in Example 1. 30.1 g product mixture was recovered. GC analysis of the mixture is reported on Table 1.

Example 8

The procedure of Example 1 was repeated. The reactor was charged with 0.05 moles, 13.5 g $NbCl_5$, 0.05 moles, 13.0 g $SnCl_4$, 2.01 moles, 40.2 g HF and 0.5 moles, 42.5 g HCC-30. The reaction mixture was heated to 120° C. and maintained and vented as in Example 1. 32.0 g product mixture was recovered. GC analysis of the mixture is reported on Table 1.

Example 9

The procedure of Example 1 was repeated. The reactor was charged with 0.03 moles, 8.1 g $NbCl_5$, 0.07 moles, 18.2 g $SnCl_4$, 2.15 moles, 42.92 g HF and 0.5 moles, 42.5 g HCC-30. The reaction mixture was heated to 120° C. and maintained and vented as in Example 1. 30.1 g product mixture was recovered. GC analysis of the mixture is reported on Table 1.

Example 10

The procedure of Example 1 was repeated. The reactor was charged with 0.05 moles, 13.5 g $NbCl_5$, 0.05 moles, 9.5 g $TiCl_4$, 2.54 moles, 50.8 g HF and 0.5 moles, 42.5 g HCC-30. The reaction mixture was heated to 120° C. and maintained and vented as in Example 1. 35.0 g product mixture was recovered. GC analysis of the mixture is reported on Table 1.

Example 11

The procedure of Example 1 was repeated. The reactor was charged with 0.05 moles, 17.9 g $TaCl_5$, 0.05 moles, 13.0 g $SnCl_4$, 2.10 moles, 42.0 g HF and 0.5 moles, 42.5 g HCC-30. The reaction mixture was heated to 120° C. and maintained and vented as in Example 1. 26.6 g product mixture was recovered. GC analysis of the mixture is reported on Table 1.

Example 12

The procedure of Example 1 was repeated. The reactor was charged with 0.05 moles, 13.5 g $TaCl_5$, 2.17 moles, 43.3 g HF and 0.5 moles, 42.5 g HCC-30. The reaction mixture was heated to 120° C. and maintained and vented as in Example 1. 28.7 g product mixture was recovered. GC analysis of the mixture is reported on Table 1.

TABLE 1

| Example | Catalyst | Catalyst Moles | HF Moles | HCC-30 Moles | Temp. (° C.) | Time (h) | Material Balance (%) | Product Analysis (area %) 32/31/30/* | Conversion HCC-30 (%) | Selectivity HFC-32 (%) |
|---|---|---|---|---|---|---|---|---|---|---|
| 1 | $SnCl_4$ | 0.1 | 2.10 | 0.5 | 130 | 5 | 99 | 25.2/65.7/ 8.3/0.8 | 91.7 | 27.4 |
| 2 | $TiCl_4$ | 0.1 | 2.09 | 0.5 | 135 | 5 | 98 | 33.6/54.7/ 11.5/0.2 | 88.5 | 38.0 |

TABLE 1-continued

| Example | Catalyst | Catalyst Moles | HF Moles | HCC-30 Moles | Temp. (° C.) | Time (h) | Material Balance (%) | Product Analysis (area %) 32/31/30/* | Conversion HCC-30 (%) | Selectivity HFC-32 (%) |
|---|---|---|---|---|---|---|---|---|---|---|
| 3 | MoCl$_5$ | 0.1 | 1.97 | 0.5 | 135 | 5 | 98 | 87/6.9/5.7/0.4 | 94.3 | 92.2 |
| 4 | NbCl$_5$ | 0.1 | 2.23 | 0.5 | 130 | 5 | 99 | 93.9/1/4.9/0.2 | 95.1 | 98.7 |
| 5 | TaCl$_5$ | 0.1 | 1.91 | 0.5 | 132 | 5 | 87 | 96.2/0.9/1.7/1.2 | 98.3 | 97.9 |
| 6 | NbCl$_5$ TaCl$_5$ | 0.07 0.03 | 2.21 | 0.5 | 120 | 5 | 100 | 99.3/0.1/0.2/0.4 | 99.8 | 99.5 |
| 7 | NbCl$_5$ SnCl$_4$ | 0.07 0.03 | 2.02 | 0.5 | 120 | 5 | 100 | 99/0.19/0.54/0.3 | 99.5 | 99.5 |
| 8 | NbCl$_5$/ SnCl$_4$ | 0.05 0.05 | 2.01 | 0.5 | 120 | 5 | 100 | 98.5/0.2/1.2/0.1 | 98.8 | 99.7 |
| 9 | NbCl$_5$/ SnCl$_4$ | 0.03 0.07 | 2.15 | 0.5 | 121 | 5 | 100 | 82.9/13.1/3.9/0.1 | 96.1 | 86.3 |
| 10 | NbCl$_5$/ TiCl$_4$ | 0.05 0.05 | 2.54 | 0.5 | 120 | 5 | 100 | 96.3/1.7/1.8/0.2 | 98.2 | 98.1 |
| 11 | TaCl$_5$/ SnCl$_4$ | 0.05 0.05 | 2.10 | 0.5 | 120 | 5 | 99.6 | 99.3/0.4/0.2/0.1 | 99.8 | 99.5 |
| 12 | TaCl$_5$/ TiCl$_4$ | 0.05 0.05 | 1.92 | 0.5 | 120 | 5 | 100 | 87.6/3.4 8.8/0.2 | 91.2 | 96.1 |

*Includes methyl chloride, 1,1,1-trifluoroethane, and chlorodifluoromethane.

Table shows that the conversion of HCC-30, selectivity for HFC-32 and quantity of HFC-32 present in the product mixture analysis is higher for the catalyst mixtures when compared to that of the separate components of the mixture. Also, all of the catalysts of the invention fluorinated HCC-30 in high conversion and selectivity.

What is claimed is:

1. A fluorination catalyst comprising a catalyst selected from the group consisting of
   (i) a mixture of a pentavalent niobium halide of the formula NbCl$_{5-y}$F$_y$ wherein y is 0 to 5 with a tetravalent tin halide of the formula SnCl$_{4-n}$F$_n$ wherein n is 0 to 4;
   (ii) a mixture of pentavalent niobium halide of the formula NbCl$_{5-y}$F$_y$ wherein y is 0 to 5 with a tetravalent titanium halide of the formula TiCl$_{4-m}$F$_m$ wherein m is 0 to 4;
   (iii) a mixture of pentavalent tantalum halide of the formula TaCl$_{5-x}$F$_x$ wherein x is 0 to 5 with a tetravalent tin halide of the formula SnCl$_{4-n}$F$_n$ wherein n is 0 to 4;
   (iv) a mixture of a pentavalent tantalum halide of the formula TaCl$_{5-x}$F$_x$ wherein x is 0 to 5 with a tetravalent titanium halide of the formula TiCl$_{4-m}$F$_m$ wherein m is 0 to 4; and
   (v) a mixture of a pentavalent niobium halide of the formula NbCl$_{5-y}$F$_y$ wherein y is 0 to 5 with a pentavalent tantalum halide of the formula TaCl$_{5-x}$F$_x$ wherein x is 0 to 5.

2. The catalyst of claim 1 wherein the catalyst is a mixture of a pentavalent niobium halide of the formula NbCl$_{5-y}$F$_y$ wherein y is 0 to 5 with a tetravalent tin halide of the formula SnCl$_{4-n}$F$_n$ wherein n is 0 to 4.

3. The catalyst of claim 1 wherein the catalyst is a mixture of a pentavalent niobium halide of the formula NbCl$_{5-y}$F$_y$ wherein y is 0 to 5 with a tetravalent titanium halide of the formula TiCl$_{4-m}$F$_m$ wherein m is 0 to 4.

4. The catalyst of claim 1 wherein the catalyst is a mixture of a pentavalent tantalum halide of the formula TaCl$_{5-x}$F$_x$ wherein x is 0 to 5 with a tetravalent tin halide of the formula SnCl$_{4-n}$F$_n$ wherein n is 0 to 4.

5. The catalyst of claim 1 wherein the catalyst is a mixture of a pentavalent tantalum halide of the formula TaCl$_{5-x}$F$_x$ wherein x is 0 to 5 with a tetravalent titanium halide of the formula TiCl$_{4-m}$F$_m$ wherein m is 0 to 4.

6. The catalyst of claim 1 wherein the catalyst is a mixture of a pentavalent niobium halide of the formula NbCl$_{5-y}$F$_y$ wherein y is 0 to 5 with a pentavalent tantalum halide of the formula TaCl$_{5-x}$F$_x$ wherein x is 0 to 5.

7. A process for fluorinating a hydrohalomethane compound comprising the step of contacting the hydrohalomethane compound with an effective amount of hydrogen fluoride in the presence of a catalytically effective amount of a catalyst in order to produce a fluorinated product mixture, the catalyst being selected from the group consisting of (i) a pentavalent molybdenum halide of the formula MoCl$_{5-z}$F$_z$ wherein z is 1 to 5; (ii) a mixture of a pentavalent niobium halide of the formula NbCl$_{5-y}$F$_y$ wherein y is 0 to 5 with a tetravalent tin halide of the formula SnCl$_{4-n}$F$_n$ wherein n is 0 to 4; (iii) a mixture of a pentavalent niobium halide of the formula NbCl$_{5-y}$F$_y$ wherein y is 0 to 5 with a tetravalent titanium halide of the formula TiCl$_{4-m}$F$_m$ wherein m is 0 to 4; (iv) a mixture of a pentavalent tantalum halide of the formula TaCl$_{5-x}$F$_x$ wherein x is 0 to 5 with a tetravalent tin halide of the formula SnCl$_{4-n}$F$_n$ wherein n is 0 to 4; (v) a mixture of a pentavalent tantalum halide of the formula TaCl$_{5-x}$F$_x$ wherein x is 0 to 5 with a tetravalent titanium halide of the formula TiCl$_{4-m}$F$_m$ wherein m is 0 to 4; and (vi) a mixture of a pentavalent niobium halide of the formula NbCl$_{5-y}$F$_y$ wherein y is 0 to 5 with a pentavalent tantalum halide of the formula TaCl$_{5-x}$F$_x$ wherein x is 0 to 5.

8. The process of claim 7 wherein the catalyst is a pentavalent molybdenum halide of the formula MoCl$_{5-z}$F$_x$ wherein z is 1 to 5.

9. The process of claim 7 wherein the catalyst is a mixture of a pentavalent niobium halide of the formula NbCl$_{5-y}$F$_y$ wherein y is 0 to 5, with a tetravalent tin halide of the formula SnCl$_{4-n}$F$_n$ wherein n is 0 to 4.

10. The process of claim 7 wherein the catalyst is a mixture of a pentavalent niobium halide of the formula NbCl$_{5-y}$F$_y$ wherein y is 0 to 5 with a tetravalent titanium halide of the formula TiCl$_{4-m}$F$_m$ wherein m is 0 to 4.

11. The process of claim 7 wherein the catalyst is a mixture of a pentavalent tantalum halide of the formula TaCl$_{5-x}$F$_x$ wherein x is 0 to 5 with a tetravalent tin halide of the formula SnCl$_{4-n}$F$_n$ wherein n is 0 to 4.

12. The process of claim 7 wherein the catalyst is a mixture of a pentavalent tantalum halide of the formula $TaCl_{5-x}F_x$ wherein x is 0 to 5 with a tetravalent titanium halide of the formula $TiCl_{4-m}F_m$ wherein m is 0 to 4.

13. The process of claim 7 wherein the catalyst is a mixture of a pentavalent niobium halide of the formula $NbCl_{5-y}F_y$ wherein y is 0 to 5 with a pentavalent tantalum halide of the formula $TaCl_{5-x}F_x$ wherein x is 0 to 5.

14. The process of claim 7 wherein the amount of catalyst is from about 2 to about 80 mole percent based on the mole percent of organics.

15. The process of claim 7 wherein the amount of catalyst is from about 5 to about 50 mole percent based on the mole percent of organics.

16. The process of claim 7 wherein the amount of catalyst is from about 10 to about 20 mole percent based on the amount of organics.

17. The process of claim 7 wherein the hydrohalomethane is of the formula $CH_xCl_yF_z$, wherein x is 1, 2 or 3, y is 1, 2 or 3, z is 0 or 1, and the sum of x, y, and z is 4.

18. The process of claim 7 wherein the hydrohalometbane is chloromethane, dichloromethane, trichloromethane, chlorofluoromethane, or dichlorofluoromethane.

19. The process of claim 7 wherein the hydrohalomethane is chloromethane.

20. The process of claim 7 wherein the hydrohalomethane is dichloromethane.

21. The process of claim 7 wherein the hydrohalomethane is trichloromethane.

22. The process of claim 7 wherein the hydrohalomethane is chlorofluoromethane.

23. The process of claim 7 wherein the hydrohalomethane is dichlorofluoromethane.

24. A process for producing difluoromethane comprising the step of contacting dichloromethane with at least two equivalents of hydrogen fluoride in the presence of a catalytically effective amount of a catalyst in order to produce a difluoromethane product mixture, the catalyst being selected from the group consisting of (i) a pentavalent molybdenum halide of the formula $MoCl_{5-z}F_z$ wherein z is 1 to 5; (ii) a mixture of a pentavalent niobium halide of the formula $NbCl_{5-y}F_y$ wherein y is 0 to 5 with a tetravalent tin halide of the formula $SnCl_{4-n}F_n$ wherein n is 0 to 4; (iii) a mixture of a pentavalent niobium halide of the formula $NbCl_{5-y}F_y$ wherein y is 0 to 5 with a tetravalent titanium halide of the formula $TiCl_{4-m}F_m$ wherein m is 0 to 4; (iv) a mixture of a pentavalent tantalum halide of the formula $TaCl_{5-x}F_x$ wherein x is 0 to 5 with tetravalent tin halides and mixed halides of the formula $SnCl_{4-n}F_n$ wherein n is 0 to 4; (v) a mixture of a pentavalent tantalum halide of the formula $TaCl_{5-x}F_x$ wherein x is 0 to 5 with a tetravalent titanium halide of the formula $TiCl_{4-m}F_m$ wherein m is 0 to 4; and (vi) a mixture of a pentavalent niobium halide of the formula $NbCl_{5-y}F_y$ wherein y is 0 to 5 with a pentavalent tantalum halide of the formula $TaCl_{5-x}F_x$ wherein x is 0 to 5.

25. The process of claim 24 wherein the catalyst is a pentavalent molybdenum halide of the formula $MoCl_{5-z}F_z$ wherein z is 1 to 5.

26. The process of claim 24 wherein the catalyst is a mixture of a pentavalent niobium halide of the formula $NbCl_{5-y}F_y$ wherein y is 0 to 5, with a tetravalent tin halide of the formula $SnCl_{4-n}F_n$ wherein n is 0 to 4.

27. The process of claim 24 wherein the catalyst is a mixture of a pentavalent niobium halide of the formula $NbCl_{5-y}F_y$ wherein y is 0 to 5 with a tetravalent titanium halide of the formula $TiCl_{4-m}F_m$ wherein m is 0 to 4.

28. The process of claim 24 wherein the catalyst is a mixture of a pentavalent tantalum halide of the formula $TaCl_{5-x}F_x$ wherein x is 0 to 5 with a tetravalent tin halide of the formula $SnCl_{4-n}F_n$ wherein n is 0 to 4.

29. The process of claim 24 wherein the catalyst is a mixture of a pentavalent tantalum halide of the formula $TaCl_{5-x}F_x$ wherein x is 0 to 5 with a tetravalent titanium halide of the formula $TiCl_{4-m}F_m$ wherein m is 0 to 4.

30. The process of claim 24 wherein the catalyst is a mixture of a pentavalent niobium halide of the formula $NbCl_{5-y}F_y$ wherein y is 0 to 5 with a pentavalent tantalum halide of the formula $TaCl_{5-x}F_x$ wherein x is 0 to 5.

31. The process of claim 24 wherein the catalysts of groups (ii) through (vi) are used in a molar ratio of from about 1:9 to about 9:1.

32. The process of claim 24 wherein the catalysts of groups (ii) through (vi) are used in a molar ratio of from about 3:7 to about 7:3.

33. The process of claim 24 wherein the catalysts of groups (ii) through (vi) are used in a molar ratio of about 1:1.

* * * * *